United States Patent [19]
DeSantis

[11] Patent Number: 5,511,556
[45] Date of Patent: Apr. 30, 1996

[54] NEEDLE CORE BIOPSY INSTRUMENT

[76] Inventor: Stephen A. DeSantis, 23802 Inverness Pl., Laguna Niguel, Calif. 92677

[21] Appl. No.: 225,594

[22] Filed: Apr. 11, 1994

[51] Int. Cl.$^6$ ................................................ A61B 10/00
[52] U.S. Cl. ................................... 128/754; 128/749
[58] Field of Search .................................. 128/749, 750, 128/751, 752, 753, 759, 757

[56] References Cited

U.S. PATENT DOCUMENTS

| | | | |
|---|---|---|---|
| Re. 34,056 | 9/1992 | Lindgren et al. | 128/754 |
| 3,561,429 | 2/1971 | Jewett et al. | 128/752 |
| 3,844,272 | 10/1974 | Banko | 128/2 B |
| 4,461,305 | 7/1984 | Cibley | 128/754 |
| 4,605,011 | 8/1986 | Naslund | 128/752 |
| 4,708,147 | 11/1987 | Haaga | 128/753 |
| 4,776,346 | 10/1988 | Beraha et al. | 128/754 |
| 4,893,635 | 1/1990 | DeGroot et al. | 128/754 |
| 4,907,598 | 3/1990 | Bauer | 128/753 |
| 4,950,265 | 8/1990 | Taylor | 128/749 X |
| 4,982,739 | 1/1991 | Hemstreet et al. | 128/753 X |
| 5,115,816 | 5/1992 | Lee | 128/749 |
| 5,159,933 | 11/1992 | Hut | 128/753 |
| 5,183,052 | 2/1993 | Terwilliger | 128/753 |
| 5,213,110 | 5/1993 | Redem et al. | 128/754 |
| 5,220,926 | 6/1993 | Jones | 128/754 |
| 5,224,470 | 7/1993 | Schnepp-Pesch | 128/753 |
| 5,241,969 | 9/1993 | Carson et al. | 128/753 |
| 5,246,011 | 9/1993 | Caillouette | 128/753 |
| 5,249,582 | 10/1993 | Taylor | 128/754 |

*Primary Examiner*—Sam Rimell
*Attorney, Agent, or Firm*—Stetina Brunda & Buyan

[57] ABSTRACT

A needle core biopsy instrument/extractor for extracting a tissue sample via needle aspiration is disclosed. The extractor comprises a first cannula having a sharpened, beveled cutting tip and biopsy reservoir formed on its distal end. The proximal end of the first cannula is in fluid communication with a conventional syringe such that when the plunger of the syringe is retracted via manipulation of the extractor, a vacuum is created within the biopsy reservoir of the first cannula. Axially mounted about the first cannula is a second cutting cannula which is designed and configured to selectively cover and uncover the distal end of the first cannula. A biasing member, preferably a spring, is provided to urge the second cannula forward about the distal end of the first cannula. The syringe, coaxially positioned first and second cannulas, and biasing member are contained within an introducer which is preferably designed and configured to be manipulated by one hand. The handle slide and lever of the device are oriented in such a way as to allow the retention of tissue via vacuum and the severing of the specimen by the second cannula to be exactly timed by cam operation.

21 Claims, 4 Drawing Sheets

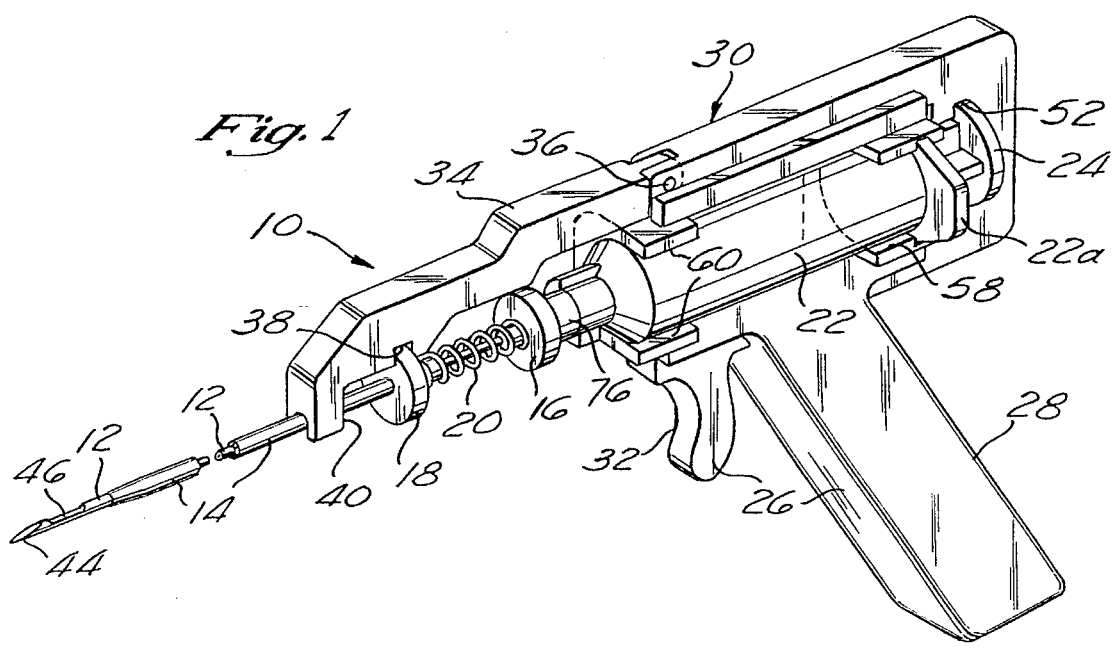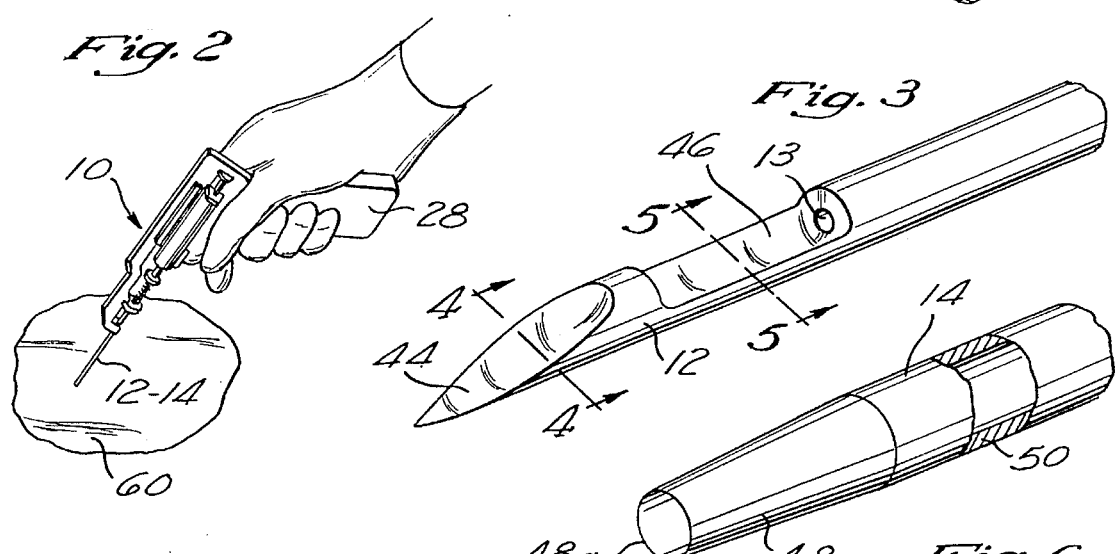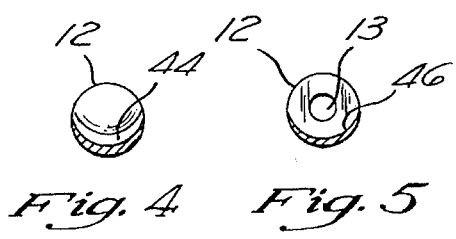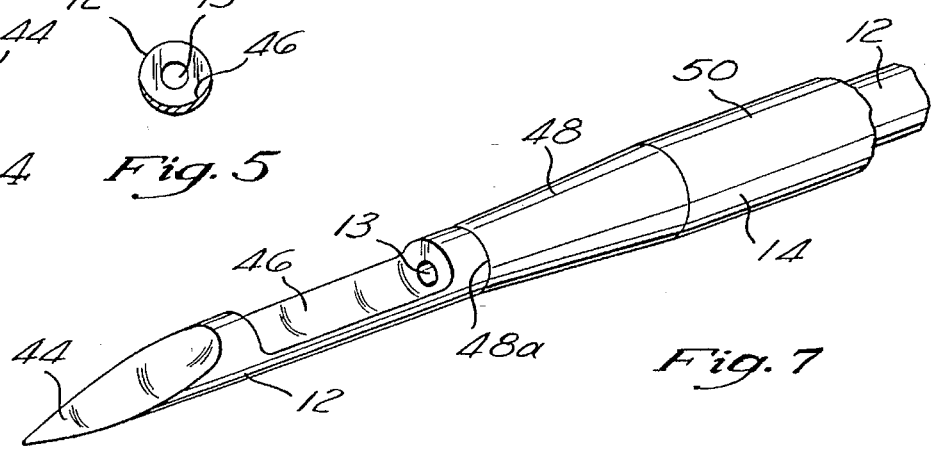

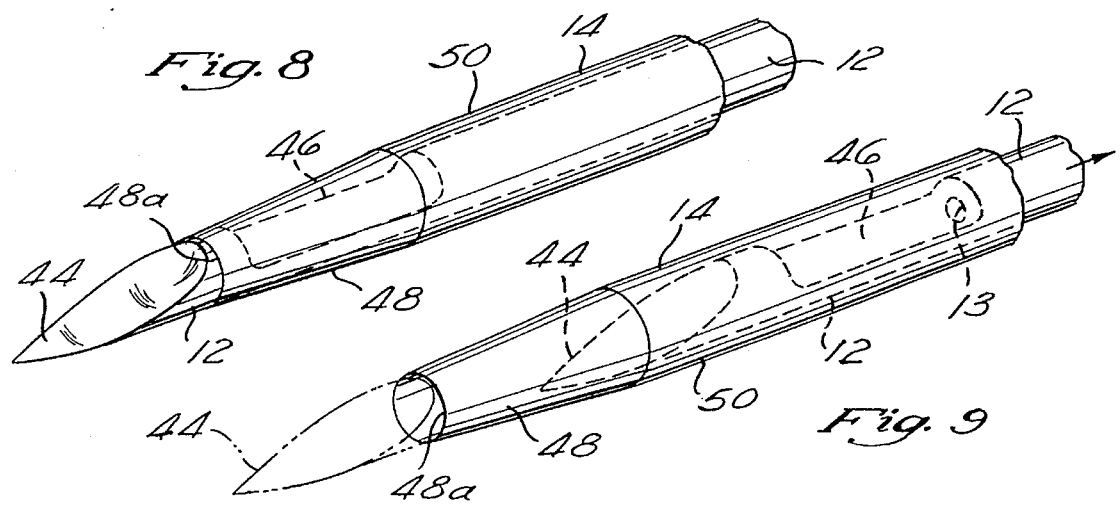
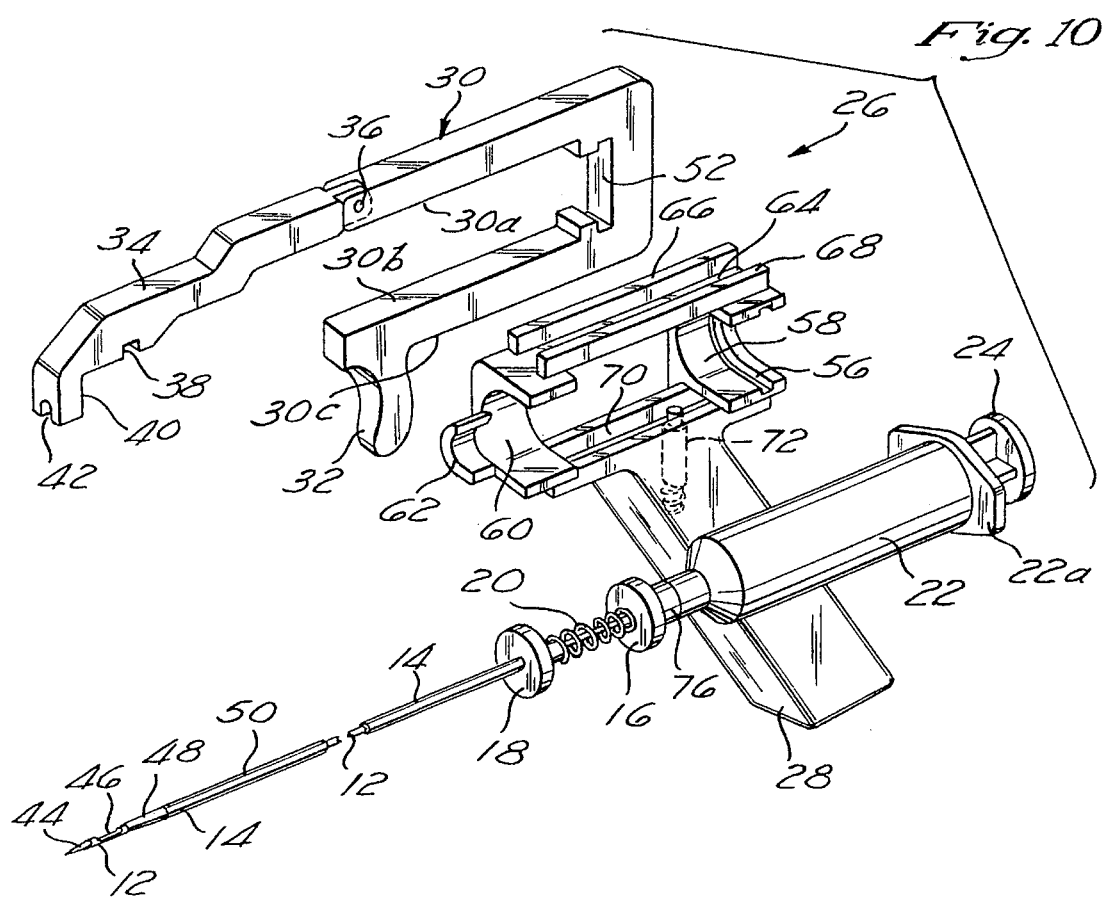

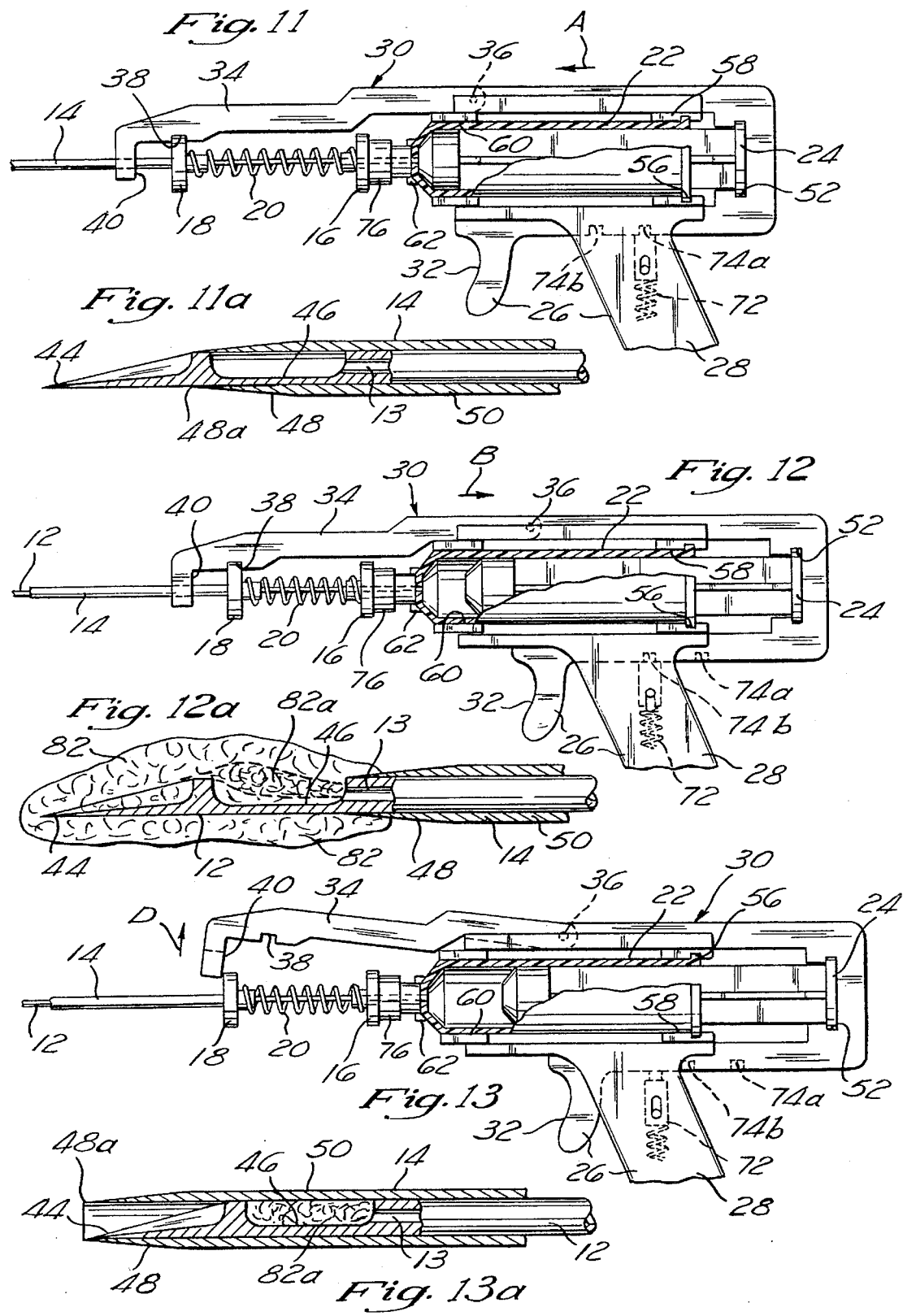

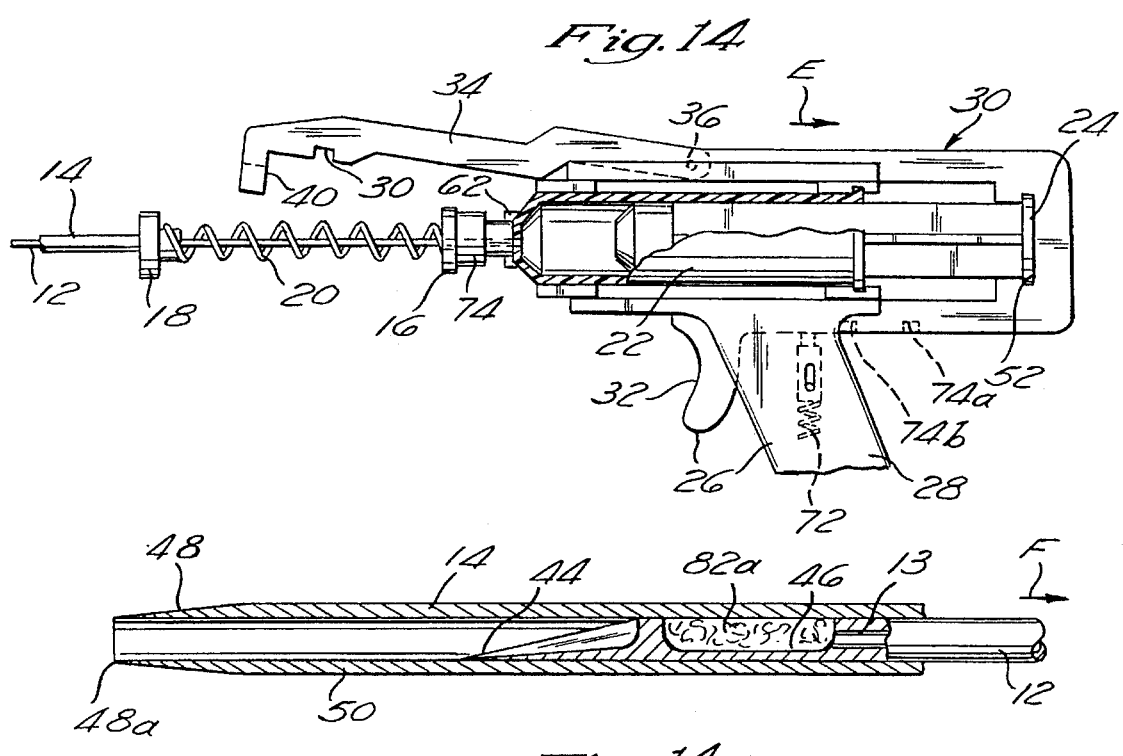

NEEDLE CORE BIOPSY INSTRUMENT

FIELD OF THE INVENTION

The present invention relates to tissue extraction devices, and more particularly, to hand-held devices for extracting tissue samples by needle aspiration.

BACKGROUND OF THE INVENTION

Biopsy devices utilizing needle aspiration to extract tissue samples are well known to those skilled in the art. Such devices are extremely useful to obtain samples of tissue suspected as being cancerous so that such tissue may be examined to confirm such suspected diagnosis. Such devices are especially used when sampling suspected cancerous tissue in the lungs, breasts, and prostate, as well as other body organs. Numerous other applications have also been found for these devices.

Generally, such biopsy instruments extract a sample of tissue from a tissue mass by either drawing a tissue sample into a hollow needle via an external vacuum force or by severing and containing a tissue sample within a notch formed on a cannula. Typical of such devices utilizing a vacuum force are U.S. Pat. No. 5,246,011 issued to Cailouette and U.S. Pat. No. 5,183,052 issued to Terwilliger. Such devices contemplate the use of advancing a hollow needle into a tissue mass and applying a vacuum force to draw a sample into the needle and hold the same therein while the tissue is extracted. Such devices, however, fail to adequately sever and contain such tissue samples as the vacuum force may not be sufficiently strong enough to sever and hold the sample within the biopsy needle.

Alternatively, other prior art biopsy instruments alternatively utilize a biopsy needle with a tissue sample recovery notch formed thereon to extract a specimen, such as described in U.S. Pat. No. 3,477,423 issued to Griffith, often referred to as the TRU-CUT needle and U.S. Pat. No. 4,776,346 issued to Beraha et al. Such devices, however, have the drawback of not effectively drawing a tissue sample of sufficient size into the biopsy notch on the cannula. Accordingly, such samples extracted by such biopsy needles may not provide sufficient tissue to perform an examination and thus require additional biopsies to be taken. Additionally, such needles have the disadvantage of having to be advanced into the desired tissue site such that the needle may possibly extend beyond the tissue site, thus resulting in the recovery of an inaccurate or non-usable tissue sample.

Further attempts in the art have tried using specially designed cannulas to enhance the cutting and recovery of tissue samples as well as combining the application of a vacuum force to draw in a tissue sample into a biopsy cavity and then cutting the tissue contained therein. U.S. Pat. No. 4,708,147 issued to Haaga discloses a cannula for a biopsy needle designed to cut a sample of tissue and then applying a vacuum to the cannula such that the tissue is drawn into the cannula and thus retained therein for recovery. Additionally, U.S. Pat. No. 3,844,272 issued to Banko discloses a biopsy device wherein a suction force, created by a vacuum, draws a sample of tissue into a receiving compartment whereby two coaxial members are rotated relative to each other so that the members essentially coact to cut off the specimen and place it into a compartment. Such combination devices, however, fail to either sufficiently isolate a sample or fail to draw in a sample of sufficient size into a biopsy compartment. Additionally, such instruments typically are difficult to maneuver and manipulate and are not necessarily accurate or effective enough to achieve their desired purpose.

Accordingly, there exists a substantial need in the art to provide a tissue sample extractor capable of effectively and efficiently drawing in a suitable sample of tissue and isolating the tissue sample within the biopsy instrument. Additionally, there is a need for a biopsy device that is easy to use and can effectively be manipulated by one hand in light of the fact that it is advantageous to perform such biopsy procedures wherein the physician user is allowed to have an additional free hand. Furthermore, there is need in the art to provide a tissue sample extractor that not only provides tissue samples of sufficient size, but allows the user to take multiple tissue samples without having to repeatedly puncture and penetrate the tissue mass.

SUMMARY OF THE INVENTION

The present invention specifically addresses and alleviates the above-mentioned deficiencies associated with the art. More particularly, the present invention comprises a tissue sample needle core biopsy needle specifically designed to allow the physician user to extract a sample of tissue in an effective and efficient manner while only requiring the user to use one hand to operate the device. The device comprises a first cannula having a specifically configured, sharpened, and beveled cutting tip and biopsy-reservoir formed at its distal end wherein the biopsy reservoir is formed proximal to the cutting tip. The first cannula is attachable to a conventional syringe such that the biopsy reservoir is in fluid communication with the barrel piston of the syringe. Axially mounted about the first cannula is a second cutting cannula, preferably having a sharpened cutting edge formed about its distal end and a shoulder attached to its proximal end. The second cannula is designed and configured to axially telescope relative the first cannula such that the second cannula selectively covers and uncovers the distal end of the first cannula. Disposed between the proximal ends of the first cannula and second cannula is a biasing member, preferably a spring, which urges the second cutting cannula to advance axially toward the distal end of the first cannula.

The syringe, the coaxially positioned first and second cannulas, and biasing member are preferably mountable within a hand-held introducer. Preferably, the introducer is comprised of two parts, namely a handle and syringe retainer and a plunger retractor member. The handle, syringe retainer, and plunger retractor member preferably cooperate to form a gun-like structure that is easy to grasp and manipulate with one hand. The handle and syringe retainer portion includes a grippable handle and means for retaining the syringe on the syringe retainer. The plunger retractor member includes a C-shaped member designed and configured to engage the plunger of the syringe. Additionally, the plunger retractor member includes a trigger-shaped member depending therefrom to enhance the grippability and function of the extractor. Furthermore, the plunger retractor member includes a cam bar that is pivotally attached to a top portion of the C-shaped member. The cam bar is preferably provided with a first cam slot and a second cam abutment surface sized and configured to selectively control the axial position of the second cannula about the first cannula. The second cannula is preferably attached to a shoulder at its proximal end that is specifically designed and configured to engage the first cam slot and second cam abutment surface. When the shoulder is engaged with the first cam slot, the distal end of the second cannula is maintained in an intermediate axial position wherein the second cannula covers the biopsy reservoir formed on the first cannula but leaves the cutting tip of the first cannula exposed. When the shoulder is allowed to advance to the second cam abutment surface, the second cannula is maintained in a distal axial position wherein the distal end of the second cannula extends just beyond the distal end of the first cannula. Additionally, the shoulder may be released altogether from the cam bar whereby the first cannula may be withdrawn from the second cannula while maintaining the second cannula resident in the patient. Such selective withdrawal of the first cannula enables multiple biopsies to be effectuated without multiple punctures of the patient's tissue mass.

In order to facilitate the selective axial positioning of the second cannula relative the first cannula, the introducer is preferably provided with a spring-activated detent or locking member and a plurality of locking apertures. Preferably, the locking member is disposed upon the handle and syringe retainer while the locking apertures are formed upon the plunger retractor member. Accordingly, the interconnection between the locking member and a respective aperture advantageously maintains the desired axial positions of the second cannula relative the first cannula whereby the second cannula is controllably axially telescoped about the first cannula. Importantly, this interconnection detachably maintains the second cannula in a proximal axial position wherein the second cannula is axially retracted about the biopsy reservoir of the first cannula. Such exposure of the biopsy reservoir ultimately enables a sample to be extracted by the extractor of the present invention.

In use, the introducer is initially maintained in an operable orientation wherein the second cannula is disposed in its intermediate axial position covering the biopsy reservoir but leaving the cutting tip of the first cannula exposed. In this position, the physician user grips the introducer and forces the coaxially positioned cannulas into the tissue mass. As the coaxially positioned cannulas advance into the tissue, the cutting tip of the first cannula selectively cuts and positions the tissue over and about the biopsy reservoir covered by the second cannula. Once positioned within the target mass, the plunger retractor member of the introducer is manually withdrawn rearwardly with respect to the handle and syringe retainer portion such that the second cannula is axially retracted to its proximal axial position wherein the biopsy reservoir of the first cannula becomes exposed to the tissue mass. Simultaneously, by such retracting or withdrawing of the plunger retractor member, the plunger of the syringe is retracted, thus creating a vacuum within the syringe that is communicated via the axial lumen of the first cannula into the biopsy reservoir. Due to the created vacuum, the cut tissue is drawn into the biopsy reservoir. Having contained the tissue therein, the cam bar of the introducer may be released from the shoulder attached to the second cannula whereupon, due to the action of the biasing member, the second cannula rapidly axially advances from the first cam slot to contact the second cam abutment surfaces of the cam bar, thus causing the second cannula to axially advance to its distal axial position. During this rapid axial advancement to the distal axial position, the cutting edge of the second cannula severs the tissue sample adjacent the biopsy reservoir and captures the same within the biopsy reservoir of the first cannula. Having thus captured the tissue sample, the introducer may then be removed and the tissue sample may be examined. Alternatively, the cam bar may be completely released from the shoulder of the second cannula thereby allowing the second cannula to remain resident within the tissue mass while withdrawing the first cannula therefrom.

In such arrangement, the second cannula may subsequently be used as a passageway through which other multiple tissue samples may be extracted without the need for further puncture of the patient.

It is therefore an object of the present invention to provide a tissue sample extractor that will effectively and efficiently remove a portion of tissue from a tissue mass.

Another object of the present invention is to provide a tissue sample extractor that extracts a sample of tissue by simultaneously drawing a sample of tissue into a biopsy reservoir, via a vacuum, and severing and containing the sample within the biopsy reservoir.

Another object of the present invention is to biopsy tissue without the need for axial advancement of a stylet into the tissue but rather, to biopsy tissue by exact placement of the covered biopsy reservoir within the tissue and eliminating any further axial movement of the same.

Another object of the present invention is to provide a tissue sample extractor that may be easily held and manipulated by one hand.

Another object of the present invention is to provide a tissue sample extractor that allows a user to take repeated tissue samples from a tissue mass without having to repeatedly puncture the tissue mass.

Another object of the present invention is to provide a tissue sample extractor which may be easily adapted for C.T. guided and/or stereoactic biopsy techniques.

Yet another object of the present invention is to provide a tissue sample extractor that is of simple construction, inexpensive to manufacture, and easy to use.

BRIEF DESCRIPTION OF THE DRAWINGS

FIG. 1 is a perspective view of a tissue sample extractor according to a preferred embodiment of the present invention;

FIG. 2 is a perspective view of the tissue sample extractor as shown in use;

FIG. 3 is a perspective view of the distal end of the first biopsy cannula of the tissue sample extractor;

FIG. 4 is a cross-sectional view taken along line 4—4 of FIG. 3;

FIG. 5 is a cross-sectional view taken along line 5—5 of FIG. 3;

FIG. 6 is a perspective view of the distal end of the second cutting cannula of the tissue sample extractor;

FIG. 7 is a perspective view of the distal ends of the first biopsy cannula and the second cutting cannula wherein the first biopsy cannula is telescoped within the second cutting cannula;

FIG. 8 is a perspective view of the first and second cannulas wherein the second cannula selectively covers a portion of the distal end of the first cannula;

FIG. 9 is a perspective view of the distal ends of the first cannula and second cannula wherein the second cannula substantially covers the distal end of the first cannula;

FIG. 10 is an exploded view of the tissue sample extractor;

FIG. 11 is a side view of the tissue sample extractor wherein the extractor is maintained in a configuration suitable for insertion into a tissue mass;

FIG. 11a is a cross-sectional view of the first and second cannulas corresponding to the position of the extractor as depicted in FIG. 11;

FIG. 12 is a side view of the extractor while positioned to obtain a sample from a tissue mass;

FIG. 12a is a cross-sectional view depicting the first and second cannulas corresponding to the position of the extractor as depicted in FIG. 12 wherein the first cannula is advanced into a tissue mass;

FIG. 13 is a side view of the extractor being maintained in a position suitable for recovery of the tissue sample;

FIG. 13a is a cross-sectional view of the first and second cannulas corresponding to the configuration maintained by the extractor in FIG. 13;

FIG. 14 is a side view of the extractor wherein the introducer has been disengaged from the second cannula and the first cannula and introducer may be removed therefrom; and FIG. 14a is a cross-sectional view of the first and second cannulas corresponding to the configuration of the extractor as depicted in FIG. 14 wherein the second cannula is maintained stationary in the patient and the first cannula may be withdrawn therefrom.

DETAILED DESCRIPTION OF THE PREFERRED EMBODIMENT

Referring to the drawings, and more particularly to FIG. 1, there is shown the needle core biopsy instrument or tissue sample extractor 10 embodying the principles of the present invention. The instrument/extractor 10 comprises a first biopsy cannula 12 that is shaped and configured to be coaxially mounted within second cutting cannula 14. Both first biopsy cannula 12 and second cutting cannula 14 have proximal and distal ends, wherein the proximal end of the first biopsy cannula 12 is attached to first shoulder 16 and the proximal end of the second cutting cannula 14 is attached to second shoulder 18.

The distal ends of first cannula 12 and second cannula 14 are more clearly depicted in FIGS. 3 and 6, respectively. The distal end of first cannula 12 includes a sharpened, beveled cutting tip 44 preferably having a gradual, upwardly extending slope that forms a shovel-type scooped shape. Such scoop-like shape advantageously allows for more efficient and less traumatic tissue penetration than other cannula cutting tips currently in use. Additionally, first cannula 12 has a hollowed-out biopsy reservoir 46, also shown in FIG. 5, formed proximal the beveled cutting tip 44. The biopsy reservoir 46 preferably is formed having a semi-circular shape that advantageously allows for relatively large, generally cylindrically-shaped tissue samples to be extracted from the tissue mass. As will be discussed in more detail infra, the distal ends of the first and second cannulas 12, 14 cooperate via relative axial movement to cut and contain a tissue sample within the biopsy reservoir 46.

At the rear portion of biopsy reservoir 46 is a lumen or channel 13 which runs the length of first cannula 12 and allows the biopsy reservoir 46 to establish fluid communication with a conventional syringe 22 via connector 76, as shown in FIG. 1. Such fluid communication between biopsy reservoir 46 and syringe 22 enhances the ability of the extractor 10 to draw in and isolate a tissue sample due to the generation of a vacuum force by the syringe 22, which shall be discussed below. The distal end of second cannula 14 is preferably formed having a hollow, frusto-conical shape that is designed and configured to allow first cannula 12 to axially pass therethrough. The distal rim 48a of the frusto-conical portion 48 is sharpened so that distal rim 48a may cut and contain a tissue sample disposed within biopsy reservoir 46 when the rim 48a is axially passed across the biopsy reservoir 46 of the first cannula 12.

As shown in FIG. 7, the distal end of first cannula 12 freely passes, via axial movement, through the distal end 48 of second cannula 14. Second cannula 14 also preferably includes a barrel section 50 that serves as a sleeve to protect and contain a biopsy sample contained within a biopsy reservoir 46 when such sample is extracted from a tissue mass. The first and second cannulas may be formed in differing lengths and diameters to be utilized for a wide variety of tissue sampling applications such as breast, prostate, deep body, lung and other soft tissue biopsies.

In addition to being coaxially positioned relative to one another, first cannula 12 and second cannula 14 are maintained in an arrangement whereby the second cannula is constantly urged forward by biasing member 20, more clearly depicted in FIG. 1. Preferably, biasing member 20 comprises a spring that is interposed between the first shoulder 16 formed on the first cannula 12 and second shoulder 18 formed on the second cannula 14. The distally urging biasing force exerted by spring 20 forces the second shoulder 18, and hence second cannula 14, to axially advance upon the first cannula 12.

In order to selectively control the position of the second cannula 14 relative to first cannula 12, the extractor 10 of the present invention advantageously incorporates the use of introducer 26. In the preferred embodiment, the introducer 26 is fabricated from polymer and/or metal materials that may be sterilized or disposed of, such materials being well known to those skilled in the art. Preferably, the introducer 26 is comprised of two parts, namely a handle and syringe retainer 28 and a plunger retractor member 30, more clearly depicted in FIG. 10. The handle and syringe retainer 28 comprises a handle portion as well as structure sized and configured for detachably interconnecting with the conventional syringe 22. More specifically, the syringe retainer 28 preferably includes first and second syringe support members 58, 60 and syringe support collar 62 which engage the syringe 22 and firmly hold the syringe 22 in position. Additionally, there is provided slot 56 that is designed and configured to detachably engage with rim 22a on syringe 22 so as to further provide secure attachment with syringe retainer 28.

The plunger retractor member 30 of introducer 26 comprises a generally C-shaped member having a trigger member 32 depending therefrom. The rear portion of the plunger retractor member 30 has a slot 52 to receive plunger 24 on syringe 22. As will be discussed, slot 52 provides means for retracting the plunger 24 such that a vacuum is created in syringe 22 and ultimately in biopsy reservoir 46 via lumen 13 shown in FIG. 3.

Mounted adjacent the top portion of the retractor member 30 is cam bar 34, which is preferably pivotally mounted 36 thereon. As more clearly illustrated in FIG. 10, the cam bar 34 includes a first cam slot 38 and a second cam abutment shoulder or surface 40. Additionally, cam bar 34 has a groove 42 which allows the coaxially positioned first cannula 12 and second cannula 14 to pass therethrough. As will be discussed, the first cam slot 38 and second cam abutment surface 40 provide means for adjusting the relative axial position of second cannula 14 with respect to first cannula 12.

The handle and syringe retainer 28 and plunger retractor member 30 are preferably connected to one another via a sliding-type engagement. More specifically, the plunger retractor member 30 is movably mounted onto the rear portion of syringe retainer 28 such that surface 30a is received upon upper guideway 64 and flanked by elongate guide members 66 and 68. Additionally, surface 30b is received within lower guideway slot 70 such that trigger member 32 protrudes from the handle and syringe retainer 28 to form a gun-type configuration. In addition, the handle and syringe retainer 28 further include a spring-activated detent or locking member 72 to engage apertures formed on surface 30c of the plunger retractor member 30, said apertures being more clearly depicted as 74a,b in FIGS. 11, 12, 13, and 14. Such spring-activated locking member 72, when aligned with locking apertures 74a,b, provide means for positioning the handle and syringe retainer 28 with respect to the plunger retractor member 30 such that desired depths and axial positioning of the cannulas 12, 14 may be more easily attained when using the extractor 10. Importantly spring-activated locking member 72, when aligned with locking aperture 74b, maintains the introducer 26 in an orientation that causes second cannula 14 to axially retract about biopsy reservoir 46 in a proximal axial position.

Having thus described the structure of the biopsy instrument/extractor 10 of the present invention, the operation of the same shall now be described with specific reference to FIGS. 11 through 14. Preparatory for use, the first and second cannulas 12 and 14 are coaxially positioned with biasing member 20 interposed between the shoulders 16 and 18. The proximal end 76 of the first cannula 12 may then be attached to the distal end of the syringe 22. As shown in FIG. 11, the syringe 22 is mounted within handle and syringe retainer 28 with plunger 24 being received in slot 52 of the plunger retractor member 30. Additionally, cam bar 34 is positioned such that second shoulder 18 is received within first cam slot 38. Additionally, the, spring-activated locking member 72 is received within locking aperture 74a in such a manner that relative orientation or position of the handle 28 and plunger retractor member 30 is maintained unless otherwise manually adjusted. FIG. 11a depicts the corresponding axial position (i.e., the intermediate axial position) between first cannula 12 and second cannula 14 while the introducer 26 is maintained in the initial orientation depicted in FIG. 11. As illustrated, the second cannula 14 selectively covers biopsy reservoir 46 while beveled cutting tip 44 axially protrudes or extend therebeyond.

While the introducer 26 and first and second cannulas 12, 14 are maintained in the orientation and relative axial position depicted in FIG. 11 and FIG. 11a, the introducer 26 is then gripped, as shown in FIG. 2, and the first and second cannulas are manually pressed or inserted into a tissue mass from which a sample is to be extracted. As mentioned above, the introducer 26, namely the combination of handle and syringe retainer 28 and plunger retractor member 30, is formed to have a gun-like shape that allows the user to manually insert the coaxially positioned cannulas 12, 14 while maintained in this intermediate axial position and ultimately extract a sample of tissue using only one hand. Such design advantageously allows the physician user to utilize their other hand so as to manipulate the tissue or perform some other function as may be required.

During insertion of the first and second cannulas 12, 14 through the tissue, the user forces both interconnected portions 28, 30 of the introducer 26 into the tissue in a direction indicated by the arrows "A" in FIG. 11. As should be noted, locking member 72 is engaged within aperture 74a during such insertion to prevent any relative axial movement between the handle 28 and plunger retractor member 30. Additionally, during such insertion the introducer 26 forces the cannulas 12, 14 into the tissue whereby the sharpened beveled cutting tip 44 is forced directly into the tissue, and the cutting tip 44 of the first cannula simultaneously cuts the tissue and positions the cut tissue adjacent its periphery so as to overlie the second cannula 14 adjacent the biopsy reservoir 46.

Once embedded within the tissue and having cut the tissue sample, the introducer 26 is manipulated such that the handle and syringe retainer 28 of the introducer 26 remains stationary while the plunger retractor member 30 is rearwardly retracted in the direction indicated by "B". The plunger retractor member 30 is retracted, via manipulation of trigger member 32, such that spring-activated locking member 72 is released (i.e., overcome) from locking aperture 74a and subsequently engage with locking aperture 74b as shown in FIG. 12. Due to the engagement of the second shoulder 18 with the cam slot 30 of the cam bar 34, during such rearward movement, the second cannula 14 axially retracts relative the first cannula 12 and is disposed in its proximal axial position wherein the biopsy reservoir 46 is exposed to the tissue mass 82, as depicted in FIG. 12a. Accordingly, the axial retraction of the frusto-conical end portion 48 of second cannula 14 allows such cut tissue mass 82 to be received within the biopsy reservoir 46. Advantageously, during such retraction of the plunger retractor member 30 relative to handle and syringe retainer 23, a vacuum is generated in syringe 22 such that the previously cut tissue mass 82 is drawn downwardly into the biopsy reservoir 46 as depicted in FIG. 12a.

Having effectively drawn the mass of tissue 82 to be extracted into the biopsy reservoir 46, the cam bar 34 is manually raised in the direction indicated by the letter "D" in FIG. 13 such that the second shoulder 18 is released from first cam slot 38. Spring member 20 preferably provides sufficient force such that upon release from first cam slot 38 the second cannula 14 rapidly axially advances with sufficient force to cause the sharpened distal end 48a of the second cannula 14 to sever and retain the tissue sample 82a to be extracted within biopsy reservoir 46. Such forward axial movement of the second cannula 12 continues until the second shoulder 18 abuts the second cam abutment surface 40. The cross-sectional view depicting this distal axial position of the second cannula 14 depicted in FIG. 13a, which corresponds with the abutment between second shoulder 18 and second cam abutment surface 40, as shown in FIG. 13. As shown, in this distal axial position, the second cannula 14 securely captures the cut tissue mass 82a within the biopsy reservoir.

Having thus isolated the tissue sample 82a from tissue mass 82, the extractor 10, and hence first and second cannulas 12, 14, may both be removed from the tissue mass by withdrawal of the extractor 10 where the tissue sample 82a may be recovered from the biopsy reservoir 46 and subsequently examined. Alternatively, as illustrated in FIG. 14, the present invention provides that cam bar 34 may be raised even further about pivot 36 to allow second shoulder 18, and thus second cannula 14, to remain in place while introducer 26, syringe 22, and first cannula 12 may be manually withdrawn in the direction indicated by the arrow "E". Advantageously, by allowing the second cannula 14 to remain stationary within tissue mass 82, the user, if desired, may make further tissue sample extractions through second cannula 14 in the manner described above. Advantageously, by using the extractor 10 of the present invention, the user will not have to make repeated punctures into the tissue which will thus facilitate the extraction of multiple samples while subjecting the subject to a less traumatic experience as compared to other devices known in the art.

There has thus been disclosed a tissue sample extractor, with various preferred embodiments thereof, having been described in detail with the various advantages being set forth. It is understood, however, that equivalents are possible and that variations in structure may be made that fall within the underlying principles of the present invention.

What is claimed is:

1. A tissue sample extractor comprising:
   a) a first biopsy cannula having proximal and distal ends, said first biopsy cannula being generally circular in cross-section and having a lumen formed therein, said distal end having a sharpened beveled cutting tip and a biopsy reservoir formed thereon, said biopsy reservoir being formed proximal said cutting tip;
   b) a second cutting cannula having proximal and distal ends, said second cutting cannula being axially mounted about said first biopsy cannula such that said first biopsy cannula is partially telescoped within said second cutting cannula, said distal end of said second cutting cannula having a sharpened cutting edge formed thereon;
   c) an introducer, said introducer being configured to simultaneously and detachably engage with said first biopsy cannula and said second cutting cannula; and
   d) wherein said introducer controllably moves said second cutting cannula about said first biopsy cannula such that said distal end of said second cutting cannula selectively covers and uncovers said distal end of said first biopsy cannula.

2. The tissue sample extractor of claim 1 wherein said introducer is configured to urge said second cutting cannula to selectively cover said biopsy reservoir and leave said sharpened beveled tip uncovered in a first intermediate position and to allow said second cutting cannula to uncover both sharpened bevel tip and biopsy reservoir in a second proximal position.

3. The tissue sample extractor of claim 2 wherein said introducer is further configured to urge said second cutting cannula to extend beyond and axially surround said distal end of said first biopsy cannula in a third distal position.

4. The tissue sample extractor of claim 3 wherein said extractor further comprises a device for creating a vacuum, said device being attached to and in fluid communication with said proximal end of said first biopsy cannula via the lumen formed therein, said device being configured to cause a vacuum to be generated within said first biopsy cannula when said second biopsy cannula is withdrawn from over the biopsy reservoir of said first cannula, said vacuum being sufficiently strong to cause a portion of said tissue to be drawn into said biopsy reservoir.

5. The tissue sample extractor of claim 4 wherein said device for creating a vacuum is interconnected with said introducer such that said introducer simultaneously causes said device for creating a vacuum to generate said vacuum when said second cutting cannula is urged into said second proximal position.

6. The tissue sample extractor of claim 3 wherein said introducer further includes an apparatus for detachably maintaining said second cutting cannula in said intermediate and distal positions.

7. The tissue sample extractor of claim 6 wherein said first biopsy cannula, said second cutting cannula, and said introducer are configured such that when said first biopsy cannula is advanced into said tissue and said second cutting cannula is withdrawn to said second proximal position, said second cutting cannula may then be advanced into said third distal position such that said second cutting cannula cuts and isolates a tissue sample within said biopsy reservoir.

8. A tissue sample extractor comprising:
   a) a first biopsy cannula having proximal and distal ends, said proximal end having a first shoulder attached thereto, said distal end having a sharpened beveled cutting tip and a biopsy reservoir formed thereon, said biopsy reservoir being formed proximal said cutting tip;
   b) a device for creating a vacuum, said device being attached to said first shoulder and in fluid communication with said biopsy reservoir of said first biopsy cannula via a vacuum conduit;
   c) a second cutting cannula having proximal and distal ends, said proximal end having a second shoulder attached thereto, said distal end having a sharpened cutting edge formed thereon, said second cutting cannula being axially mounted about said first biopsy cannula such that said first biopsy cannula is partially telescoped within said second cutting cannula;
   d) a biasing member disposed between said first shoulder and said second shoulder such that said second shoulder urges said second cutting cannula to distally advance about said first biopsy cannula; and
   e) an introducer, said introducer being detachably engaged with said device for creating a vacuum and said second shoulder of said second cutting cannula, said introducer being attached to said second cutting cannula and said device for creating a vacuum such that said introducer controllably adjusts the relative positions of said first and second cannulas such that said distal end of said second cutting cannula is selectively movable about said first biopsy cannula.

9. The tissue sample extractor of claim 8 wherein:
   a) said device for creating a vacuum comprises a conventional syringe and plunger;
   b) said biasing member disposed between said first shoulder and said second shoulder comprises a spring member; and
   c) said introducer comprises a handle and syringe retainer in combination with a plunger retractor member, said handle, said syringe retainer, and said plunger retractor member cooperating to form a gun-like member.

10. The tissue sample extractor of claim 9 wherein said plunger retractor member comprises a generally C-shaped member having a trigger-shaped member depending therefrom and a slot formed thereon to engage said plunger, said generally C-shaped member having a cam bar pivotally attached along a top portion thereof, said cam bar having a first cam slot and a second cam abutment surface, said first cam slot and said second cam abutment surface being configured to detachably engage with said second shoulder of said second cutting cannula, said first cam slot and said second cam abutment surface being spaced such that said second cutting cannula is urged forward about said first biopsy cannula such that said distal end of said first biopsy cannula is selectively covered by said second cutting cannula.

11. The tissue sample extractor of claim 10 wherein:
   a) said first cam slot detachably engages said second shoulder such that said second cutting cannula selectively covers said biopsy reservoir and leaves said sharpened beveled cutting tip uncovered; and
   b) said second cam abutment surface detachably engages said second shoulder such that said second cutting cannula covers both said biopsy reservoir and said sharpened beveled cutting tip.

12. The tissue sample extractor of claim 11 wherein said introducer may be used by a single hand.

13. The tissue sample extractor of claim 12 wherein said biasing member and said introducer cooperate to allow said first biopsy cannula to advance through said second cutting cannula such that said biopsy reservoir and sharpened beveled cutting tip are exposed when said first biopsy cannula and said second cutting cannula are inserted into a tissue mass.

14. The tissue sample extractor of claim 13 wherein said cam bar is configured to be manually adjustable such that said second shoulder is urged from said first cam slot to said second cam abutment surface, said cam bar being further manually adjustable such that said second shoulder is releasably from said second cam abutment surface such that said cutting cannula is configured to be axially removable from said second cutting cannula.

15. The tissue sample extractor of claim 14 wherein when said first biopsy cannula and said second cutting cannula are embedded within a tissue mass and said biopsy reservoir is exposed by withdrawal of second cutting cannula, said cam bar is manually adjustable such that said biasing member forces said second cutting cannula to distally advance over said biopsy reservoir of said first biopsy cannula wherein said distal advancement forces said second cutting cannula to sever a portion of said tissue and contain said portion within said biopsy reservoir.

16. The tissue sample extractor of claim 15 wherein said cam bar is further configured to be manually adjustable such that said biasing member forces said second cutting cannula to become embedded within said tissue mass, said second cutting cannula being so embedded that at least one additional sample of tissue may be extracted through said second cutting cannula.

17. The tissue sample extractor as recited in claim 4 wherein said device for creating a vacuum comprises a disposable syringe.

18. A method for extracting a sample of tissue from a tissue mass, the method comprising the steps of:

a) inserting a first and a second cannula within the tissue mass, said first cannula being partially telescoped within said second cannula, said first cannula having a sharpened beveled cutting tip and a biopsy reservoir formed at a distal end thereof, said second cannula having a sharpened cutting edge formed about a distal end thereof, said first cannula being so telescoped within said second cannula such that said sharpened beveled butting tip protrudes from said second cannula while said biopsy reservoir remains covered by said second cannula;

b) withdrawing said second cutting cannula to expose biopsy reservoir in said first cannula by manipulating a trigger on a C-shaped retraction member;

c) simultaneously applying a vacuum force to the interior of said fist cannula such that a sample of tissue is drawn into said biopsy reservoir, a cam then causing the retraction member to release the second cutting cannula, thereby allowing a biasing member to axially advance said second cannula about said first cannula such that said second cutting cannula severs said tissue collected about said biopsy reservoir and encases said sample within said biopsy reservoir; and d) removing said sample encased within said biopsy reservoir.

19. The method of claim 1 further comprising the step of simultaneously withdrawing said second cannula relative to said first cannula and causing said vacuum to be produced within said first cannula.

20. The method of claim 1 wherein the step of applying a vacuum force comprises applying a vacuum force via a conventional syringe.

21. The method of claim 1 wherein said introducer is configured to be used by a single hand of the user.

\* \* \* \* \*